(12) United States Patent
Ooms et al.

(10) Patent No.: US 8,173,762 B2
(45) Date of Patent: *May 8, 2012

(54) PROCESS FOR THE PREPARATION OF POLYCARBONATE

(75) Inventors: Pieter Ooms, Krefeld (DE); Andreas Bulan, Langenfeld (DE); Johann Rechner, Kempen (DE); Rainer Weber, Odenthal (DE); Marc Buts, Duffel (BE); Johan Vanden Eynde, Zwijnaarde (BE)

(73) Assignee: Bayer MaterialScience AG, Leverkusen (DE)

( * ) Notice: Subject to any disclaimer, the term of this patent is extended or adjusted under 35 U.S.C. 154(b) by 32 days.

This patent is subject to a terminal disclaimer.

(21) Appl. No.: 12/829,845

(22) Filed: Jul. 2, 2010

(65) Prior Publication Data

US 2011/0009592 A1    Jan. 13, 2011

(30) Foreign Application Priority Data

Jul. 7, 2009 (DE) .................. 10 2009 032 020

(51) Int. Cl.
*C08G 64/00* (2006.01)
*C08G 63/02* (2006.01)

(52) U.S. Cl. ................... 528/196; 528/198; 528/200

(58) Field of Classification Search .......... 528/196, 528/198, 200

See application file for complete search history.

(56) References Cited

U.S. PATENT DOCUMENTS

| | | | |
|---|---|---|---|
| 2,991,273 A | 7/1961 | Hechelhammer et al. | |
| 2,999,835 A | 9/1961 | Goldberg | |
| 2,999,846 A | 9/1961 | Schnell et al. | |
| 3,148,172 A | 9/1964 | Fox | |
| 3,271,367 A | 9/1966 | Schnell et al. | |
| 4,016,190 A | 4/1977 | Böckmann et al. | |
| 4,764,308 A | 8/1988 | Sauer et al. | |
| 4,982,014 A | 1/1991 | Freitag et al. | |
| 5,104,723 A | 4/1992 | Freitag et al. | |
| 5,126,428 A | 6/1992 | Freitag et al. | |
| 5,227,458 A | 7/1993 | Freitag et al. | |
| 5,734,004 A | 3/1998 | Kühling et al. | |
| 6,340,736 B1 | 1/2002 | Coenen et al. | |
| 6,531,623 B2 | 3/2003 | Chrisochoou et al. | |
| 6,548,691 B2 | 4/2003 | Alewelt et al. | |
| 6,680,400 B2 | 1/2004 | Alewelt et al. | |
| 6,713,035 B1 | 3/2004 | Iwanaga et al. | |
| 7,442,835 B2 | 10/2008 | Keggenhoff et al. | |
| 2002/0095020 A1 | 7/2002 | Hucks et al. | |
| 2005/0118088 A1 | 6/2005 | Olbert et al. | |
| 2008/0053836 A1 | 3/2008 | Bulan et al. | |
| 2010/0324256 A1* | 12/2010 | Ooms et al. | 528/200 |

FOREIGN PATENT DOCUMENTS

| | | |
|---|---|---|
| CA | 2126336 A1 | 7/1993 |
| CA | 2375245 A1 | 12/2000 |
| DE | 1570703 A1 | 2/1970 |
| DE | 2036052 A1 | 1/1972 |
| DE | 2063050 A1 | 7/1972 |
| DE | 2211956 A1 | 10/1973 |
| DE | 3327274 A1 | 2/1985 |
| DE | 3832396 A1 | 2/1990 |
| DE | 3833953 A1 | 4/1990 |
| DE | 102006041465 A1 | 3/2008 |
| EP | 0784048 A1 | 7/1997 |
| EP | 0881986 B1 | 1/2000 |
| EP | 1216981 A2 | 6/2002 |
| EP | 1216982 A2 | 6/2002 |
| EP | 1219589 A1 | 7/2002 |
| EP | 1221454 A1 | 7/2002 |
| EP | 1640341 A2 | 3/2006 |
| EP | 1894914 A2 | 3/2008 |
| FR | 1561518 A | 3/1969 |
| GB | 583477 A | 12/1946 |
| GB | 1122003 A | 7/1968 |
| GB | 1229482 A | 4/1971 |
| GB | 1341318 A | 12/1973 |
| GB | 1367790 A | 9/1974 |
| WO | WO-93/13084 A1 | 7/1993 |
| WO | WO-96/16898 A1 | 6/1996 |
| WO | WO-97/30932 A1 | 8/1997 |
| WO | WO-00/78682 A1 | 12/2000 |
| WO | WO-01/38419 A1 | 5/2001 |
| WO | WO-03/007639 A1 | 1/2003 |
| WO | WO-03/072237 A1 | 9/2003 |

* cited by examiner

*Primary Examiner* — Terressa Boykin
(74) *Attorney, Agent, or Firm* — Conolly Bove Lodge & Hutz LLP

(57) ABSTRACT

A combined process for the preparation of polycarbonate from bisphenols and diaryl carbonates, the monophenol liberated being reacted again for the preparation of the diaryl carbonate and the alkali metal halide forming in the preparation of the diaryl carbonate being converted by electrochemical oxidation, optionally over a gas diffusion electrode, into chlorine and alkali hydroxide solution, the chlorine being recycled into the preparation of the phosgene and the alkali hydroxide solution being recycled into the preparation of the diaryl carbonate.

11 Claims, 1 Drawing Sheet

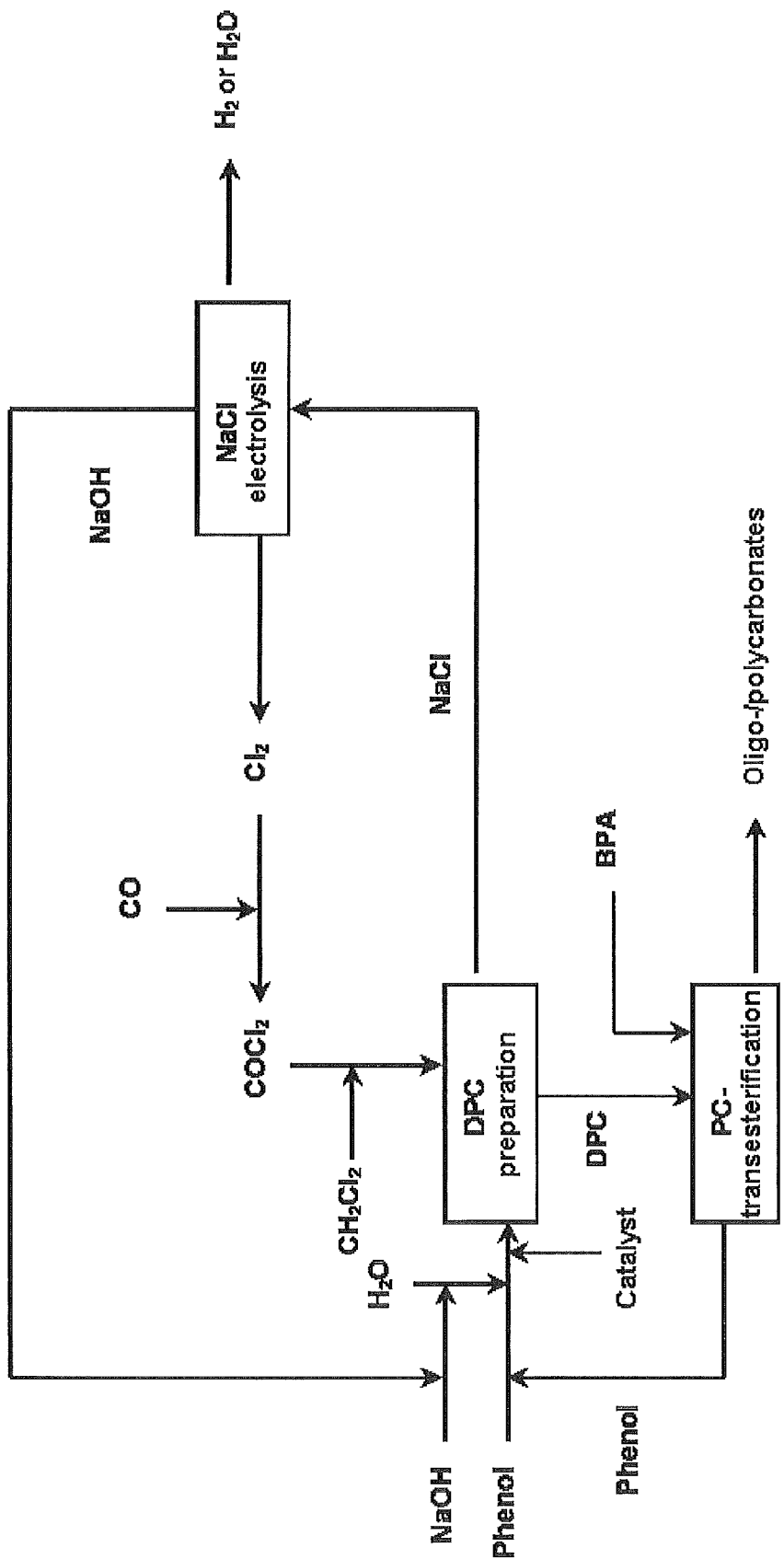

PROCESS FOR THE PREPARATION OF POLYCARBONATE

RELATED APPLICATIONS

This application claims benefit to German Patent Application No. 10 2009 032 020.2, filed Jul. 7, 2009, which is incorporated herein by reference in its entirety for all useful purposes.

BACKGROUND OF THE INVENTION

The invention relates to a combined process for the preparation of polycarbonate from bisphenols and diaryl carbonates, the monophenol liberated being reacted with phosgene again for the preparation of the diaryl carbonate, and the alkali metal halide forming in the preparation of the diaryl carbonate being converted by electrochemical oxidation into chlorine, the chlorine being recycled to the preparation of the phosgene. The alkali solution likewise formed can be used again for the preparation of the diaryl carbonate.

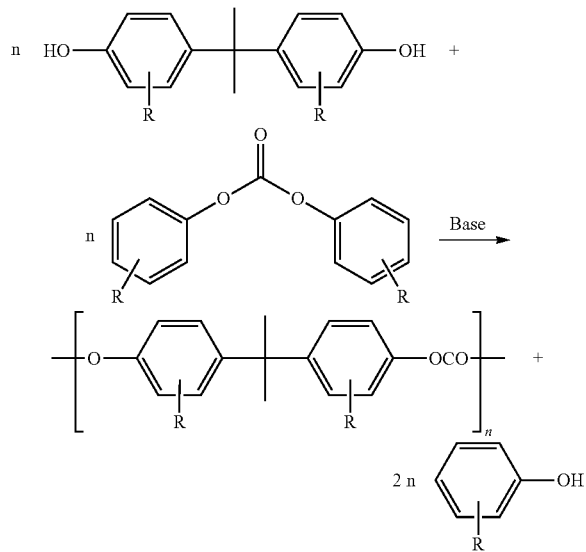

The preparation of aromatic polycarbonates by the melt transesterification process is known and is described, for example, in "Schnell", Chemistry and Physics of Polycarbonates, Polymer Reviews, Vol. 9, Interscience Publishers, New York, London, Sydney 1964, in D. C. Prevorsek, B. T. Debona and Y. Kersten, Corporate Research Center, Allied Chemical Corporation, Moristown, N.J. 07960, "Synthesis of Poly(ester)carbonate Copolymers" in Journal of Polymer Science, Polymer Chemistry Edition, Vol. 19, 75-90 (1980), in D. Freitag, U. Grigo, P. R. Müller, N. Nouvertne, BAYER AG, "Polycarbonates" in Encyclopedia of Polymer Science and Engineering, Vol. 11, Second Edition, 1988, pages 648-718 and finally in Dres. U. Grigo, K. Kircher and P. R. Müller "Polycarbonate" in Becker/Braun, Kunststoff-Handbuch [Plastics Handbook], Volume 3/1, Polycarbonate, Polyacetale, Polyester, Celluloseester [Polycarbonates, Polyacetals, Polyesters, Cellulose esters], Carl Hanser Verlag, Munich, Vienna 1992, pages 117-299.

WO 93/13085 A1 describes a process for the preparation of polycarbonate, in which the monophenol which was liberated in the transesterification process can be reacted with a carbonyl dihalide (e.g. phosgene) to give the diaryl carbonate again. In this process, the carbonyl dihalide is prepared from CO and a metal halide compound. This method of preparation via a catalyst is complicated and uneconomical.

The preparation of the diaryl carbonate used in the melt transesterification process for aromatic polycarbonates, for example by the phase boundary process, is described in principle in the literature, cf. for example in Chemistry and Physics of Polycarbonates, Polymer Reviews, H. Schnell, Vol. 9, John Wiley and Sons, Inc. (1964), pages 50/51.

U.S. Pat. No. 4,016,190 A describes a process for the preparation of diaryl carbonates which is operated at temperatures of >65° C. In this process, the pH is initially set low (pH 8 to 9) and then high (10 to 11).

Optimizations of the process by improving the mixing and maintaining a narrow temperature and pH profile as well as isolation of the product are described in EP 1 219 589 A1, EP 1 216 981 A2, EP 1 216 982 A2 and EP 784 048 A1.

In these known processes, however, a high residual phenol value in the waste water of these processes, which may pollute the environment and present the waste water treatment plants with an increased waste water problem, necessitates complicated purification operations. Thus, WO 0307639 A1 describes a removal of the organic impurities in the waste water by an extraction with methylene chloride.

According to known processes, the sodium chloride-containing solution is freed from solvents and organic residues and then disposed of.

According to WO 2000/078682 A1 or U.S. Pat. No. 6,340,736 A, the sodium chloride-containing waste waters can be purified by ozonolysis and then used in the sodium chloride electrolysis. A disadvantage of this process is the very expensive ozonolysis.

EP 1 894 914 A2 describes the recycling of sodium chloride-containing waste water from the diaryl carbonate preparation by phase boundary phosgenation of sodium phenolate (DPC) through a chloralkali electrolysis with an increase in the sodium chloride concentration by separation of the reaction waste water from the wash phases and increased water transport by a novel membrane technology. However, reuse of monophenols, alkali solution and halide formed in the process has not been described.

Starting from the prior art described above, it is the object to provide a polycarbonate preparation process which gives products in high purity and good yield and permits reduction of the environmental pollution or waste water problem in the waste water treatment plants by maximized recycling of byproducts and process waste water solutions which originate from the polycarbonate production.

Furthermore, in the recycling, the conversion of sodium chloride into chlorine and sodium hydroxide solution and optionally hydrogen should be effected with minimum use of energy and therefore the protection of resources.

EMBODIMENTS OF THE INVENTION

An embodiment of the present invention is a process for preparing oligocarbonate and/or polycarbonate comprising:
  a) transesterifying a bisphenol with a diaryl carbonate to obtain an oligocarbonate and/or polycarbonate and a monophenol;
  b) isolating or separating said oligocarbonate and/or polycarbonate from said monophenol;
  c) reacting said monophenol in the presence of an alkali solution with a carbonyl dihalide and separating the resulting products, wherein said products comprise an alkali metal halide and a diaryl carbonate, wherein said diaryl carbonate is reused in step a);

d) electrochemically oxidating said alkali metal halide obtained in step c) to obtain a halogen and an alkali solution;

e) reacting at least a portion of said halogen from step d) with carbon monoxide to obtain a carbonyl dihalide, wherein at least a portion of said carbonyl dihalide is used in step c);

f) reusing at least a portion of said alkali solution obtained in step d) in step c).

Another embodiment of the present invention is the above process, wherein said bisphenol used in step a) is a dihydroxydiarylalkane of formula (I)

HO—Z—OH    (I)

wherein Z is a divalent organic radical comprising from 6 to 30 carbon atoms, wherein said divalent organic radical comprises an aromatic group.

Another embodiment of the present invention is the above process, wherein said diaryl carbonate used in step a) is a di-$C_6$-$C_{14}$-aryl ester.

Another embodiment of the present invention is the above process, wherein said monophenol used in step c) is a phenol of formula (II)

(II)

[structure: phenyl ring with R substituent and OH]

wherein
R is hydrogen, halogen, or a branched or straight-chain $C_1$- to $C_9$-alkyl radical or alkoxycarbonyl radical.

Another embodiment of the present invention is the above process, wherein said diaryl carbonate is diphenyl carbonate, said bisphenol is bisphenol A, said carbonyl dihalide is phosgene, and said alkali solution is sodium hydroxide solution.

Another embodiment of the present invention is the above process, wherein said alkali metal halide in step c) is sodium chloride and the electrolysis of said sodium chloride in step d) produces sodium hydroxide solution and chlorine and is effected using a gas diffusion electrode as a cathode.

Another embodiment of the present invention is the above process, wherein said products in step c) comprises an alkali halide-containing waste water which is separated prior to step d) from solvent residues and optionally catalyst residues.

Another embodiment of the present invention is the above process, wherein said separation is achieved via extraction or stripping of the solution with steam, neutralization, and/or treatment with an adsorbent.

The process of claim 8, wherein said neutralization is achieved using hydrogen chloride or hydrochloric acid and said adsorbent is active carbon Another embodiment of the present invention is the above process, wherein said alkali halide-containing waste water is concentrated prior to step d).

Another embodiment of the present invention is the above process, wherein said alkali halide-containing waste water is concentrated prior to step d) via osmotic distillation with sodium hydroxide solution as a water acceptor.

BRIEF DESCRIPTION OF THE DRAWINGS

FIG. 1 schematically depicts a combined process for the preparation of polycarbonate from bisphenol A and diphenyl carbonate, the phenol separated off being reacted again with phosgene for the preparation of the diphenyl carbonate and the sodium chloride forming in the preparation of the diphenyl carbonate being converted by electrochemical oxidation into chlorine and the chlorine being recycled to the preparation of the phosgene.

DESCRIPTION OF THE INVENTION

The present invention therefore relates to a process for the preparation of solvent-free polycarbonate, starting from bisphenols and diaryl carbonates, which is characterized in that the monophenol which is liberated in the reaction to give oligo-/polycarbonate is used again for the preparation of the aromatic diaryl carbonate, the alkali metal halide forming in the preparation of the diaryl carbonate being converted by electrolysis into the halogen and this in turn, after isolation and reaction with carbon monoxide, being converted into the carbonyl dihalide, which is then used again with the alkali solution likewise formed in the electrolysis and the monophenol for the preparation of the diaryl carbonate.

The overall process according to the invention is therefore flexible, easy to carry out and gives products in high purity, which are extremely important for the overall process, with simultaneous reduction of the environmental pollution by reuse of monophenols, alkali solution and halide forming in the process.

The process according to the invention comprises at least the following process steps:
  a) transesterification of one or more bisphenols with one or more diaryl carbonates to give the oligo-/polycarbonate and the monophenol,
  b) isolation or separation of the polycarbonate and of the monophenol,
  c) reaction of the monophenol in the presence of alkali solution with the carbonyl dihalide and separation of the products, the diaryl carbonate being reused in step a),
  d) electrochemical oxidation of the alkali metal halide obtained in step c) to give halogen and alkali solution,
  e) reaction of at least a part of the halogen from step d) with carbon monoxide to give the carbonyl dihalide, which in turn is at least partly used in step c),
  f) reuse of at least a part of the alkali solution from d) in step c).

Bisphenols suitable for the process according to the invention are dihydroxydiarylalkanes of the formula (I)

HO—Z—OH    (I)

in which Z is a divalent organic radical having 6 to 30 carbon atoms which contains one or more aromatic groups. Examples of such compounds which can be used in step a) of the process according to the invention are dihydroxydiarylalkanes, such as hydroquinone, resorcinol, dihydroxybiphenyl, bis(hydroxyphenyl)alkanes, bis(hydroxyphenyl)cycloalkanes, bis(hydroxyphenyl) sulphides, bis(hydroxyphenyl) ethers, bis(hydroxyphenyl) ketones, bis(hydroxyphenyl) sulphones, bis(hydroxyphenyl) sulphoxides, a,a'-bis(hydroxyphenyl)diisopropylbenzenes and the compounds thereof which are alkylated, alkylated on the nucleus and halogenated on the nucleus.

Preferred bisphenols are 4,4'-dihydroxybiphenyl, 2,2-bis (4-hydroxyphenyl)-1-phenylpropane, 1,1-bis(4-hydroxyphenyl)phenylethane, 2,2-bis(4-hydroxyphenyl)propane (bisphenol A (BPA)), 2,4-bis(4-hydroxyphenyl)-2-methylbutane, 1,3-bis[2-(4-hydroxyphenyl)-2-propyl]benzene (bisphenol M), 2,2-bis(3-methyl-4-hydroxyphenyl)propane, bis(3,5-dimethyl-4-hydroxyphenyl)methane, 2,2-bis(3,5-dimethyl-4-hydroxyphenyl)propane, bis(3,5-dimethyl-4-hydroxyphenyl)sulphone, 2,4-bis(3,5-dimethyl-4-hydroxyphenyl)-2-methylbutane, 1,3-bis[2-(3,5-dimethyl-4-hydroxyphenyl)-2-propyl]benzene, 1,1-bis(4-hydroxyphenyl)cyclohexane and 1,1-bis(4-hydroxyphenyl)-3,3,5-trimethylcyclohexane (bisphenol TMC).

Particularly preferred bisphenols are 4,4'-dihydroxybiphenyl, 1,1-bis(4-hydroxyphenyl)phenylethane, 2,2-bis(4-hydroxyphenyl)propane (bisphenol A (BPA)], 2,2-bis(3,5-dimethyl-4-hydroxyphenyl)propane, 1,1-bis(4-hydroxyphenyl)cyclohexane and 1,1-bis(4-hydroxyphenyl)-3,3,5-trimethylcyclohexane (bisphenol TMC).

Suitable bisphenols are described, for example, in U.S. Pat. No. 2,999,835 A, U.S. Pat. No. 3,148,172 A, U.S. Pat. No. 2,991,273 A, U.S. Pat. No. 3,271,367 A, U.S. Pat. No. 4,982,014 A and U.S. Pat. No. 2,999,846 A, in the German Offenlegungsschriften (German Published Specifications) DE 15 70 703 A, DE 20 63 050 A, DE 20 36 052 A, DE 22 11 956 A and DE 38 32 396 A, French Patent FR 1 561 518 A, in the monograph by H. Schnell, Chemistry and Physics of Polycarbonates, Interscience Publishers, New York 1964, page 28 et seq.; page 102 et seq., and by D. G. Legrand, J. T. Bendler, Handbook of Polycarbonate Science and Technology, Marcel Dekker New York 2000, page 72 et seq.

In the case of the preparation, according to the invention, of homopolycarbonates, only one bisphenol is used; in the case of the preparation, according to the invention, of copolycarbonates, a plurality of bisphenols are used, it of course being possible for the bisphenols used as well as all other chemicals and auxiliaries added to the synthesis to be contaminated with the impurities originating from their own synthesis, handling and storage, although it is desirable to work with raw materials which are as pure as possible.

It should be emphasized here that the process according to the invention can be used practically for all known bisphenols.

Diaryl carbonates which can be used in step a) of the process according to the invention are di-$C_6$-$C_{14}$-aryl esters, preferably the diesters of phenol or substituted phenols, i.e. diphenyl carbonate or, for example, bissalicyl carbonate. The diaryl carbonates are used in 1.01 to 1.30 mol, preferably in 1.02 to 1.15 mol, based on 1 mol of diphenol.

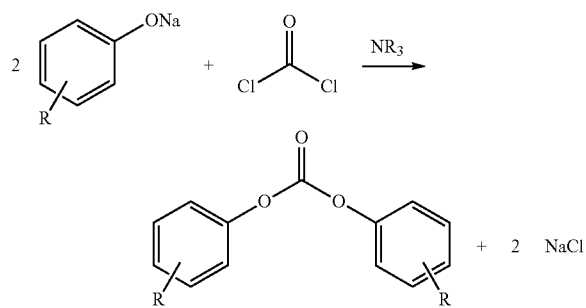

The completely reacted, at least two-phase reaction mixture, containing at most traces of (<2 ppm) aryl chlorocarbonates is allowed to settle by phase separation. The aqueous alkaline phase (reaction waste water) is separated off and the organic phase is extracted with dilute hydrochloric acid and water. The combined water phases are fed to the waste water work-up, where solvent and catalyst fractions are separated off by stripping or extraction and are recycled. Thereafter, after a certain pH of, for example, 6 to 8 has been established, for example by addition of hydrochloric acid, any organic impurities still remaining, such as, for example, monophenol, are removed by treatment with active carbon and fed to the chloralkali electrolysis.

In another preferred variant of the work-up, the reaction waste water is not combined with the wash phases but, after stripping or extraction for separating off solvents and catalyst residues, is adjusted to a certain pH of, for example, 6 to 8, for example by addition of hydrochloric acid, and, after the still remaining organic impurities, such as, for example, monophenol, have been separated off by treatment with active carbon, is fed to the chloralkali electrolysis.

After removal of the solvent and catalyst fractions by stripping or extraction, the wash phases can optionally be fed back to the synthesis.

The preparation of the diaryl carbonates is effected in a known manner by reaction of monophenols and phosgene in an inert solvent in the presence of alkali and a nitrogen catalyst by the phase boundary process with formation of alkali metal halide (NaCl). Optimizations of the process by improvement of the mixing and maintenance of a narrow temperature and pH profile as well as isolation of the diaryl carbonate are described in EP 1 219 589 A1, EP 1 216 981 A2, EP 1 216 982 A2 and EP 784 048 A1.

Particularly suitable monophenols for the preparation of the diaryl carbonates in step c) are phenols of the formula (II)

(II)

in which
R is hydrogen, halogen or a branched or straight-chain $C_1$- to $C_9$-alkyl radical or alkoxycarbonyl radical.

Phenol, alkylphenols, such as cresols, p-tert-butylphenol, p-cumylphenol, p-n-octylphenol, p-isooctylphenol, p-n-nonylphenol and p-isononylphenol, halophenols, such as p-chlorophenol, 2,4-dichlorophenol, p-bromophenol and 2,4,6-tribromophenol, or methyl salicylate are therefore preferred. Phenol is particularly preferred.

The alkali used for formation of the phenolate may be an alkali solution with hydroxides from the series: Na, K, Li hydroxide; sodium hydroxide solution is preferred and is preferably used as 10 to 55% strength by weight solution in the novel process.

The reaction b) can be accelerated by catalysts, such as tertiary amines, N-alkylpiperidines or onium salts. Tributylamine, triethylamine and N-ethylpiperidine are preferably used.

The amine catalyst used may be open-chain or cyclic; triethylamine and ethylpiperidine are particularly preferred. The catalyst is preferably used as a 1 to 55% strength by weight solution in the novel process.

Here, onium salts are understood as meaning compounds such as $NR_4X$, it being possible for R to be an alkyl and/or aryl radical and/or an H and X being an anion.

In process step b), phosgene can be used in liquid or gaseous form or in solution in an inert solvent.

Inert organic solvents which can preferably be used in step b) in the novel process are, for example, dichloromethane, toluene, the various dichloroethanes and chloropropane compounds, chlorobenzene and chlorotoluene. Dichloromethane is preferably used.

The polycarbonates can be modified in a conscious and controlled manner by the use of small amounts of chain terminators and branching agents. Suitable chain terminators and branching agents are known from the literature. Some are described, for example, in DE-A 38 33 953. Preferably used chain terminators are phenol or alkylphenols, in particular phenol, p-tert-butylphenol, isooctylphenol, cumylphenol, the chlorocarbonic acid esters thereof or acid chlorides of monocarboxylic acids or mixtures of these chain terminators. Preferred chain terminators are phenol, cumylphenol, isooctylphenol, para-tert-butylphenol.

Examples of compounds suitable as branching agents are aromatic or aliphatic compounds having more than three, preferably three or four, hydroxyl groups. Particularly suitable examples having three or more than three phenolic hydroxyl groups are phloroglucinol, 4,6-dimethyl-2,4,6-tri (4-hydroxyphenyl)hept-2-ene, 4,6-dimethyl-2,4,6-tri(4-hydroxyphenyl)heptane, 1,3,5-tri(4-hydroxyphenyl)benzene, 1,1,1-tri(4-hydroxyphenyl)ethane, tri(4-hydroxyphenyl)phenylmethane, 2,2-bis(4,4-bis(4-hydroxyphenyl)cyclohexyl] propane, 2,4-bis(4-hydroxyphenylisopropyl)phenol, tetra(4-hydroxyphenyl)methane.

Examples of other trifunctional compounds suitable as branching agents are 2,4-dihydroxybenzoic acid, trimesic acid, cyanuric chloride and 3,3-bis(3-methyl-4-hydroxyphenyl)-2-oxo-2,3-dihydroindole.

Particularly preferred branching agents are 3,3-bis(3-methyl-4-hydroxyphenyl)-2-oxo-2,3-dihydroindole and 1,1,1-tri(4-hydroxyphenyl)ethane.

The 0.05 to 2 mol %, based on bisphenols used, of branching agents which are optionally to be concomitantly used can be used together with the bisphenols.

It should be noted that the reaction components for the first step, the transesterification, i.e. the bisphenols and the diaryl carbonates, are free of alkali metal and alkaline earth metal ions, amounts of less than 0.1 ppm of alkali metal and alkaline earth metal ions being tolerable. Such pure bisphenols or diaryl carbonates are obtainable by recrystallizing, washing or distilling the bisphenols or diaryl carbonates. In the process according to the invention, the content of alkali metal and alkaline earth metal ions, both in the bisphenol and in the diaryl carbonate, should be a value of <0.1 ppm.

The transesterification reaction of the bisphenol and of the diaryl carbonate in the melt is preferably carried out in two stages. In the first stage, the melting of the bisphenol and of diaryl carbonate takes place at temperatures of 80-250° C., preferably 100-230° C., particularly preferably 120-190° C., under atmospheric pressure in 0-5 hours, preferably 0.25-3 hours. After addition of the catalyst, the oligocarbonate is prepared from the bisphenol and the diaryl carbonate by applying a vacuum (up to 2 mmHg) and increasing the temperature (up to 260° C.), by distilling off the monophenol. The oligocarbonate thus prepared has an average molecular weight $M_w$ (determined by measuring the relative solution viscosity in dichloromethane or in mixtures of equal amounts by weight of phenol/o-dichlorophenol, calibrated by light scattering) in the range of 2000 to 18 000, preferably of 4000 to 15 000. Here, the main amount of monophenol (80%) is recovered from the process.

In the second stage, the polycarbonate is prepared in the polycondensation by further increasing the temperature to 250-320° C., preferably 270-295° C., and a pressure of <2 mmHg. Here, the residue of monophenols is recovered. Small losses of monophenols of <5%, preferably <2%, particularly preferably <1%, may occur, caused by end groups in the polycarbonate and residual monophenol in the polycarbonate. These losses must be compensated by corresponding amounts of monophenol for the preparation of the diaryl carbonate.

Catalysts in the context of the process according to the invention for the transesterification in step a) are all inorganic or organic basic compounds, for example lithium, sodium, potassium, caesium, calcium, barium, magnesium hydroxides, carbonates, halides, phenolates, diphenolates, fluorides, acetates, phosphates, hydrogen phosphates, boranates, nitrogen and phosphorus bases, such as, for example, tetramethylammonium hydroxide, tetramethylammonium acetate, tetramethylammonium fluoride, tetramethylammonium tetraphenylboranate, tetraphenylphosphonium fluoride, tetraphenylphosphonium tetraphenylboranate, dimethyldiphenylammonium hydroxide, tetraethylammonium hydroxide, DBU, DBN or guanidine systems, such as, for example, 1,5,7-triazabicyclo-[4,4,0]dec-5-ene, 7-phenyl-1,5,7-triazabicyclo[4,4,0]dec-5-ene, 7-methyl-1,5,7-triazabicyclo[4,4,0]dec-5-ene, 7,7'-hexylidenedi-1,5,7-triazabicyclo[4,4,0]dec-5-ene, 7,7'-decylidenedi-1,5,7-triazabicyclo[4,4,0]dec-5-ene, 7,7'-dodecylidenedi-1,5,7-triazabicyclo[4,4,0]dec-5-ene, or phosphazenes, such as, for example, the phosphazene base $P_1$-t-Oct=tert-octyliminotris(dimethylamino)phosphorane, the phosphazene base $P_1$-t-Butyl=tert-butyliminotris(dimethylamino)phosphorane, BEMP=2-tert-butylimino-2-diethylamino-1,3-dimethylperhydro-1,3,2-diaza-2-phosphorane.

The catalysts are used in amounts of $10^{-2}$ to $10^{-8}$ mol, based on 1 mol of bisphenol.

The catalysts can also be used in combination (two or more) with one another.

With the use of alkali metal/alkaline earth metal catalysts, it may be advantageous to add the alkali metal/alkaline earth metal catalysts at a later time (for example after the oligocarbonate synthesis during the polycondensation in the second stage). The addition of the alkali metal/alkaline earth metal catalyst can be effected, for example, as a solid or as a solution in water, phenol, oligocarbonate or polycarbonate.

The concomitant use of alkali metal or alkaline earth metal catalysts does not contradict the abovementioned requirement for purity of the reactants.

The reaction of the bisphenol and the diaryl carbonate to give the polycarbonate can be carried out batchwise or preferably continuously in the context of the process according to the invention, for example in stirred tanks, thin-film evaporators, falling-film evaporators, stirred tank cascades, extruders, kneaders, simple disc reactors and disc reactors for high viscosity substances.

The aromatic polycarbonates of the process according to the invention should have average molecular weights $M_w$ of 18 000 to 80 000, preferably 19 000 to 50 000, determined by measuring the relative solution viscosity in dichloromethane or in mixtures of equal amounts by weight of phenol/o-dichlorobenzene, calibrated by light scattering.

It is advantageous to purify the monophenols eliminated from the transesterification of the bisphenol and of the diaryl carbonate to give the polycarbonate and isolated, prior to the use in the diaryl carbonate synthesis. The crude monophenols which are isolated in the transesterification process may be contaminated, inter alia, with diaryl carbonates, the bisphenol, salicylic acid, isopropenylphenol, phenyl phenoxybenzoate, xanthone or the hydroxymonoaryl carbonate, depending on transesterification conditions and distillation conditions. The purification can be effected by the customary purification processes, i.e. for example distillation or recrystallization. The purity of the monophenols is then >99%, preferably >99.8%, particularly preferably >99.95%.

The preparation of phosgene from carbon monoxide and chlorine in step a) is known per se, for example from EP 881 986 B1 or EP 1 640 341 A. The reaction of the carbon monoxide is effected by reacting carbon monoxide with chlorine to give phosgene, for example over an active carbon catalyst. Alternative catalysts can, however, also be used. Reference may be made here to the prior art (e.g. DE 332 72 74; GB 583 477; WO 97/30932; WO 96/16898; U.S. Pat. No. 6,713,035). On the industrial scale, phosgene is produced predominantly by reacting carbon monoxide with chlorine, preferably over active carbon as a catalyst. The strongly exothermic gas-phase reaction takes place at temperatures of at least 100° C. to not more than 600° C., as a rule in tube-bundle reactors. The heat of reaction can be removed in various ways, for example by a liquid heat-exchange agent, as described, for example, in WO 03/072237, or by evaporative cooling via a secondary circulation with simultaneous use of heat of reaction for steam generation, as disclosed, for example, in U.S. Pat. No. 4,764,308. Preferably, active carbon is used as the catalyst in step a), the active carbon having a total sulphur content of less than 1% by weight, in particular less than 0.5% by weight, based on the total weight of the catalyst. Furthermore, step a) according to the invention is preferably carried out at temperatures of less than or equal to 300° C. and furthermore step a) according to the invention is combined in combination with the generation of steam. Furthermore, the catalyst preferably has a specific surface area of greater than 10 m$^2$/g after step a).

The electrolysis of the alkali metal chloride-containing solution in step d) can be effected directly after solvent residues and optionally catalyst residues have been separated off, in particular by extraction or stripping of the solution with steam, neutralization, in particular with hydrogen chloride or hydrochloric acid, and treatment with adsorbents, in particular with active carbon.

Membrane electrolysis methods (cf. in this context Peter Schmittinger, CHLORINE, Wiley-VCH Verlag, 2000) are usually used, for example for the electrolysis of sodium chloride-containing solutions. The electrolysis can be effected optionally with increased water transport and optionally with the use of a gas diffusion electrode as a cathode, as described in DE 10 2006 041 465 A1.

A further preferred process variant is that water is withdrawn from the alkali metal chloride-containing waste water from c) prior to the electrolysis d) by a concentration method. This can be effected by evaporation or membrane methods.

According to WO 01/38419 A, the sodium chloride-containing solution can be evaporated down by means of thermal methods, so that a highly concentrated sodium chloride solution can be fed to the electrolysis cells. However, the evaporation is energy-intensive and expensive.

It is also possible to use, for example, reverse osmosis or particularly preferably membrane distillation or membrane contactors (cf. MELIN; RAUTENBACH, Membranverfahren [Membrane methods]; SPRINGER, BERLIN, 2003). A disadvantage here is the high energy requirement for overcoming the high osmotic pressures, with the result that cost efficiency is no longer achieved.

A process characterized in that the alkali metal chloride-containing solution from c) is concentrated prior to the electrolysis d) by means of membrane distillation methods is therefore particularly preferred.

The concentration of NaCl solutions by osmotic distillation is energy-saving, particularly when the NaOH solution originating from the NaCl electrolysis is used as water acceptor. This has advantages particularly when a dilute sodium hydroxide solution is used in the diaryl carbonate production, it then additionally being possible to save the water for the dilution of the sodium hydroxide solution.

The osmotic distillation takes place by molecular and optionally Knudsen diffusion of water vapour through a membrane. The diffusion rate is thus dependent on the difference between the water vapour pressures on the two sides of the membrane and the porosity, thickness and sinuousness thereof.

In order to permit efficient concentration, a concentrated solution of an alkali metal hydroxide, preferably sodium hydroxide or potassium hydroxide, particularly preferably sodium hydroxide, should be used as the water acceptor.

By combination of the operation of the electrolysis cells and concentration methods, the sodium chloride can be virtually quantitatively recovered from the waste water of the diphenyl carbonate preparation.

FIG. 1 schematically shows a combined process for the preparation of polycarbonate from bisphenol A and diphenyl carbonate, the phenol separated off being reacted again with phosgene for the preparation of the diphenyl carbonate and the sodium chloride forming in the preparation of the diphenyl carbonate being converted by electrochemical oxidation into chlorine and the chlorine being recycled to the preparation of the phosgene. The alkali solution likewise resulting can be reused for the preparation of the diphenyl carbonate. In the case of concentration of the sodium chloride-containing waste water solution prior to the electrolysis by osmotic distillation using a concentrated sodium hydroxide solution as a water acceptor, additional water can be used again for diluting the sodium hydroxide solution for the diphenyl carbonate preparation.

The examples are intended to illustrate the process according to the invention on the basis of the polycarbonate preparation with recycling of the phenol to the preparation of diphenyl carbonate and electrolysis of the resulting sodium chloride-containing waste water phases to give chlorine and sodium hydroxide solution, which can be used again for the diphenyl carbonate preparation process.

All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

Example 1 a) Preparation of Polycarbonate

From a storage vessel, 8600 kg/h of melt mixture consisting of 4425 kg/h of diphenyl carbonate (20 658 mol/h) and 4175 kg/h of bisphenol A (18 287 mol/h), with addition of 0.52 kg of the phenol adduct of tetraphenylphosphonium phenolate with 65.5% of tetraphenylphosphonium phenolate/h (0.786 mol/h; i.e. 0.0043 mol %) dissolved in 4.5 kg of phenol/h, are pumped through a heat exchanger, heated to 190° C. and passed through a hold-up column at 12 bar and 190° C. The average residence time is 50 minutes.

The melt is then passed via a relief valve into a separator at 200 mbar. The outflowing melt is heated to 189° C. again in a falling-film evaporator at 200 mbar and is collected in a receiver. After a residence time of 20 minutes, the melt is pumped into the next three, identically set-up stages. The conditions in the 2nd/3rd/4th stage are 100/74/40 mbar, 218/

251/276° C. and 20 minutes/10 minutes/10 minutes. The resulting oligomer has a relative viscosity of 1.09. All vapours are passed via pressure regulating means into a column under vacuum and are removed as condensates.

Thereafter, the oligomer is condensed in a downstream basket reactor at 278° C. and 3.0 mbar for a residence time of 45 minutes to give a relatively high molecular weight product. The relative viscosity is 1.195. The vapours are condensed.

A partial stream of 150 kg/h of melt is branched off by means of a gear pump from the melt stream which is passed into a further basket reactor, 185 g/h of a 5% strength aqueous phosphoric acid are added, stirring is effected via a static mixer having a length-to-diameter ratio of 20 and the mixture is recycled into the main melt stream. Directly after combination, the phosphoric acid is homogeneously distributed in the total melt stream by means of a further static mixer.

The melt thus treated is further exposed to the process conditions in a further basket reactor at 284° C., 0.7 mbar and for an average residence time of 130 minutes, discharged and granulated.

The vapours are condensed in the vacuum unit and behind it.

The polycarbonate obtained has the following characteristics: relative viscosity 1.201/phenolic OH 255 [ppm]/DPC 71 [ppm]/BPA 6 [ppm]/phenol 56 [ppm]. The phenol distilled off can be recycled into the diphenyl carbonate preparation.

b) Preparation and Working Up of Diphenyl Carbonate

A mixture of 145.2 kg/h of 14.5% strength sodium hydroxide solution, prepared by dilution of 65.8 kg/h of a 32.0% strength sodium hydroxide solution with 79.4 kg/h of demineralized water, and 48.3 kg/h of fresh and/or recovered phenol was continuously combined with a solution of 86.2 kg/h of methylene chloride and 27.5 kg/h of phosgene (8 mol % excess, based on phenol) in an upright, cooled tubular reactor. This reaction mixture was cooled to a temperature of 33° C., and a pH of 11.5 was measured after an average residence time of 15 seconds. 5.4 kg/h 50.0% strength NaOH were metered into this reaction mixture in the second stage of the process so that the pH of the second reaction stage was 8.5 after a further residence time of 5 minutes. In the second stage of the process, the reaction mixture was continuously mixed by being passed through a tube provided with constrictions. After further addition of NaOH, the reaction temperature was adjusted to 30° C. by cooling. After the organic phase had been separated from the aqueous phase (reaction waste water), the DPC solution was washed with 0.6% strength hydrochloric acid and water. After removal of the solvent, 99.9% strength diphenyl carbonate was obtained. The reaction waste water was not combined with the wash phases and was freed from solvent residues and catalyst by stripping with steam. After neutralization (pH 7) with hydrochloric acid and treatment with active carbon, the reaction waste water contained 17.0% of NaCl and <2 ppm of phenol.

The waste water could be fed to the electrochemical oxidation without further purification.

c) Electrochemical Oxidation of the Reaction Waste Water from b)

The electrolysis was carried out in a laboratory electrolysis cell having an anode area of 0.01 m². The current density was 4 kA/m², the outflow temperature on the cathode side was 88° C. and the outflow temperature on the anode side was 89° C. An electrolysis cell having a standard anode and cathode coating from DENORA, Germany, was used. An ion exchange membrane from DuPont, Nafion 982 WX, was used. The electrolysis voltage was 3.02 V. A sodium chloride-containing solution was circulated by pumping at a mass flow rate of 0.8 kg/h through the anode chamber. The concentration of the solution fed to the anode chamber was 25.0% by weight of NaCl. An 18.6% strength by weight NaCl solution could be removed from the anode chamber. 0.133 kg/h of a 17.0% strength by weight reaction waste water from the diphenyl carbonate preparation from Example 1b) and 0.0655 kg/h of solid sodium chloride were added to the NaCl solution removed from the anode chamber. The solution was then fed back into the anode chamber. The water transport via the membrane was 3.5 mol of water per mole of sodium.

On the cathode side, a sodium hydroxide solution was circulated by pumping at a mass flow rate of 0.653 kg/h. The concentration of the sodium hydroxide solution fed into the cathode side was 30.0% by weight of NaOH, and the sodium hydroxide solution removed from the cathode side had a concentration of 33.0% of NaOH. 0.180 kg/h of the 33.0% strength alkali was removed from the volume stream, and the remainder was made up with 0.060 kg/h of water and recycled into the cathode element.

25.8% of the sodium chloride reacted originated from the DPC reaction waste water.

Example 2 a) Preparation of Polycarbonate

The polycarbonate was prepared as described in 1a).

b) Preparation and Working Up of Diphenyl Carbonate

The procedure was as described in Example 1b), but the reaction waste water was combined with the wash phases to give a total process waste water and was freed from solvent residues and catalyst by stripping with steam. After neutralization with hydrochloric acid and treatment with active carbon, the total process waste water contained 13.0% of NaCl and <2 ppm of phenol.

The waste water could be fed to the electrochemical oxidation without further purification.

c) Electrochemical Oxidation of the Total Process Waste Water from 2b)

The electrolysis was carried out in a laboratory electrolysis cell having an anode area of 0.01 m². The current density was 4 kA/m², the outflow temperature on the cathode side was 88° C. and the outflow temperature on the anode side was 89° C. An electrolysis cell having a standard anode and cathode coating from DENORA, Germany, was used. An ion exchange membrane from DuPont, Nafion 982 WX, was used. The electrolysis voltage was 3.02 V. A sodium chloride-containing solution was circulated by pumping at a mass flow rate of 0.8 kg/h through the anode chamber. The concentration of the solution fed to the anode chamber was 25.0% by weight of NaCl. An 18.6% strength by weight NaCl solution could be removed from the anode chamber. 0.127 kg/h of a 13.0% strength by weight reaction waste water from the diphenyl carbonate preparation from Example 2b) and 0.0717 kg/h of solid sodium chloride were added to the NaCl solution removed from the anode chamber. The solution was then fed back into the anode chamber. The water transport via the membrane was 3.5 mol of water per mole of sodium.

On the cathode side, a sodium hydroxide solution was circulated by pumping at a mass flow rate of 0.653 kg/h. The concentration of the sodium hydroxide solution fed into the cathode side was 30.0% by weight of NaOH, and the sodium hydroxide solution removed from the cathode side had a concentration of 33.0% of NaOH. 0.180 kg/h of the 33.0% strength alkali was removed from the volume stream, and the remainder was made up with 0.060 kg/h of water and recycled into the cathode element.

18.8% of the sodium chloride reacted originated from the DPC total process waste water.

Example 3 a) Preparation of Polycarbonate

The polycarbonate was prepared as described in 1a).

b) Preparation of Diphenyl Carbonate

The diphenyl carbonate was prepared according to the process described in 1b) and the reaction waste water was separated off and treated. The reaction waste water could be fed to the electrochemical oxidation without further purification.

c) Electrochemical Oxidation of the Reaction Waste Water Using Gas Diffusion Electrodes Since no hydrogen is required for the preparation of DPC, the formation of hydrogen in the electrolysis can be dispensed with. The electrolysis was therefore operated with gas diffusion electrodes. The current density was 4 kA/m$^2$, the outflow temperature on the cathode side was 88° C. and the outflow temperature on the anode side was 89° C. An electrolysis cell having a standard anode coating from DENORA, Germany, was used. An ion exchange membrane from DuPont, Nafion 982 WX, was used. The electrolysis voltage was 2.11 V. The sodium chloride concentration of the solution removed from the anode chamber was 17.0% by weight of NaCl. 0.178 kg/h of 17.0% strength by weight reaction waste water and 0.0579 kg/h of solid sodium chloride were added to the NaCl solution removed from the anode chamber. The solution was then fed back into the anode chamber. The water transport via the membrane was 4.9 mol of water per mole of sodium.

On the cathode side, a sodium hydroxide solution was circulated by pumping at a mass flow rate of 0.653 kg/h. The concentration of the sodium hydroxide solution fed into the cathode side was 30.0% by weight of NaOH, and the sodium hydroxide solution removed from the cathode side had a concentration of 31.5% by weight of NaOH. 0.189 kg/h of the 31.5% strength alkali was removed from the volume stream, the remainder was made up with 0.0312 kg/h of water and recycled into the cathode element.

The proportion of reacted sodium chloride from the DPC reaction waste water was 34.4%.

The invention claimed is:

1. A process for preparing oligocarbonate and/or polycarbonate comprising:
   a) transesterifying a bisphenol with a diaryl carbonate to obtain an oligocarbonate and/or polycarbonate and a monophenol;
   b) isolating or separating said oligocarbonate and/or polycarbonate from said monophenol;
   c) reacting said monophenol in the presence of an alkali solution with a carbonyl dihalide and separating the resulting products, wherein said products comprise an alkali metal halide and a diaryl carbonate, wherein said diaryl carbonate is reused in step a);
   d) electrochemically oxidating said alkali metal halide obtained in step c) to obtain a halogen and an alkali hydroxide solution;
   e) reacting at least a portion of said halogen from step d) with carbon monoxide to obtain a carbonyl dihalide, wherein at least a portion of said carbonyl dihalide is used in step c);
   f) reusing at least a portion of said alkali hydroxide solution obtained from step d) in step c).

2. The process of claim 1, wherein said bisphenol used in step a) is a dihydroxydiarylalkane of formula (I)

wherein Z is a divalent organic radical comprising from 6 to 30 carbon atoms, wherein said divalent organic radical comprises an aromatic group.

3. The process of claim 1, wherein said diaryl carbonate used in step a) is a di-$C_6$-$C_{14}$-aryl ester.

4. The process of claim 1, wherein said monophenol used in step c) is a phenol of formula (II)

wherein
R is hydrogen, halogen, or a branched or straight-chain $C_1$- to $C_9$-alkyl radical or alkoxycarbonyl radical.

5. The process of claim 1, wherein said diaryl carbonate is diphenyl carbonate, said bisphenol is bisphenol A, said carbonyl dihalide is phosgene, and said alkali solution is sodium hydroxide solution.

6. The process of claim 5, wherein said alkali metal halide in step c) is sodium chloride and the electrolysis of said sodium chloride in step d) produces sodium hydroxide solution and chlorine and is effected using a gas diffusion electrode as a cathode.

7. The process of claim 1, wherein said products in step c) comprises an alkali halide-containing waste water which is separated prior to step d) from solvent residues and optionally catalyst residues.

8. The process of claim 7, wherein said separation is achieved via extraction or stripping of the solution with steam, neutralization, and/or treatment with an adsorbent.

9. The process of claim 8, wherein said neutralization is achieved using hydrogen chloride or hydrochloric acid and said adsorbent is active carbon.

10. The process of claim 7, wherein said alkali halide-containing waste water is concentrated prior to step d).

11. The process of claim 10, wherein said alkali halide-containing waste water is concentrated prior to step d) via osmotic distillation with sodium hydroxide solution as a water acceptor.

* * * * *